(12) United States Patent
Lancelle et al.

(10) Patent No.: US 11,344,392 B2
(45) Date of Patent: *May 31, 2022

(54) COMPUTER IMPLEMENTED METHOD FOR MODIFYING A DIGITAL THREE-DIMENSIONAL MODEL OF A DENTITION

(71) Applicant: Ivoclar Vivadent AG, Schaan (LI)

(72) Inventors: Marcel Lancelle, Zürich (CH); Roland Mörzinger, Attersee am Attersee (AT); Nicolas Degen, Erlenbach (CH); Gábor Sörös, Budapest (HU); Bartolovic Nemanja, Zürich (CH)

(73) Assignee: Ivoclar Vivadent AG, Schaan (LI)

( * ) Notice: Subject to any disclaimer, the term of this patent is extended or adjusted under 35 U.S.C. 154(b) by 0 days.

This patent is subject to a terminal disclaimer.

(21) Appl. No.: 16/922,375

(22) Filed: Jul. 7, 2020

(65) Prior Publication Data
US 2020/0330200 A1    Oct. 22, 2020

Related U.S. Application Data

(63) Continuation of application No. 16/278,444, filed on Feb. 18, 2019, now Pat. No. 10,779,917.

(30) Foreign Application Priority Data

Feb. 20, 2018  (EP) ..................... 18157574
Feb. 21, 2018  (EP) ..................... 18157809
Sep. 28, 2018  (EP) ..................... 18197512

(51) Int. Cl.
*A61C 13/00*    (2006.01)
*A61C 13/34*    (2006.01)
(Continued)

(52) U.S. Cl.
CPC .............. *A61C 13/34* (2013.01); *A61B 90/36* (2016.02); *A61C 5/77* (2017.02); *A61C 9/004* (2013.01);
(Continued)

(58) Field of Classification Search
CPC ....... A61C 13/34; A61C 9/0046; A61C 9/004; A61C 5/77; A61C 9/0053; A61C 7/002;
(Continued)

(56) References Cited

U.S. PATENT DOCUMENTS

6,068,482 A * 5/2000 Snow ................ A61C 7/00
433/223
6,845,175 B2 * 1/2005 Kopelman .............. A61B 6/14
128/922

(Continued)

*Primary Examiner* — Said Broome
(74) *Attorney, Agent, or Firm* — Ann M. Knab; Thad McMurray (57) ABSTRACT

The present invention relates to a computer implemented method for modifying a digital three-dimensional model (3) of a dentition comprising:
  displaying an image of the dentition by applying a virtual camera to the three-dimensional model to render the image for a display (1);
  acquiring a line drawn by a user on the image on the display (1);
  projecting the acquired line, using the virtual camera (4), to a three-dimensional projection surface (7) approximating the shape of the dental arches and extending the upper and lower dental arches to cover any opening therebetween;
  obtaining visible teeth arch contour curves, namely incisal curve and gingiva border curve, of the upper and lower teeth arches, and projecting the teeth arch contour curves to the projection surface;
  selecting one of the teeth arch contour curves as teeth arch contour curve to be modified and selecting the other
(Continued)

teeth arch contour curve of the same teeth arch or a curve derived therefrom as a baseline curve;

deforming all teeth belonging to the selected contour curve to be modified along the projected line in the three-dimensional model of the dentition in a length direction such that at least parts of the selected contour curve to be modified, after deformation and projection to the projection surface, coincide with the projected line and any remaining parts of the selected contour curve to be modified are located between the projected line and the baseline curve, whereas the baseline curve remains unaffected by the deformation.

15 Claims, 3 Drawing Sheets

(51) Int. Cl.
| | | |
|---|---|---|
| *A61C 5/77* | (2017.01) | |
| *A61C 9/00* | (2006.01) | |
| *A61B 90/00* | (2016.01) | |
| *G16H 30/40* | (2018.01) | |
| *G06T 17/20* | (2006.01) | |
| *G06T 19/20* | (2011.01) | |
| *A61C 7/00* | (2006.01) | |
| *B33Y 80/00* | (2015.01) | |
| *G16H 50/50* | (2018.01) | |
| *A61B 5/00* | (2006.01) | |

(52) U.S. Cl.
CPC .......... *A61C 9/0046* (2013.01); *A61C 9/0053* (2013.01); *A61C 13/0019* (2013.01); *G06T 17/20* (2013.01); *G06T 19/20* (2013.01); *G16H 30/40* (2018.01); *A61B 5/4547* (2013.01); *A61B 2090/365* (2016.02); *A61C 7/002* (2013.01); *A61C 13/0004* (2013.01); *B33Y 80/00* (2014.12); *G06T 2207/30036* (2013.01); *G06T 2210/41* (2013.01); *G06T 2219/2016* (2013.01); *G06T 2219/2021* (2013.01); *G16H 50/50* (2018.01)

(58) Field of Classification Search
CPC ......... G16H 30/40; G06T 17/20; G06T 19/20; G06T 2210/41; G06T 2219/2016; G06T 2219/2021; G06T 2207/30036
See application file for complete search history.

(56) References Cited

U.S. PATENT DOCUMENTS

| | | | |
|---|---|---|---|
| 7,613,527 B2* | 11/2009 | Raby | G16H 50/50 |
| | | | 700/17 |
| 7,717,708 B2 | 5/2010 | Sachdeva et al. | |
| 8,348,665 B2* | 1/2013 | Kuo | A61C 7/08 |
| | | | 433/24 |
| 9,439,608 B2* | 9/2016 | Schutyser | A61C 9/0046 |
| 9,775,491 B2 | 10/2017 | Clausen et al. | |
| 2011/0212420 A1 | 9/2011 | Vuillemot | |
| 2013/0060532 A1 | 3/2013 | Clausen et al. | |
| 2013/0158958 A1 | 6/2013 | Methot | |
| 2017/0319293 A1 | 11/2017 | Fisker | |
| 2017/0367792 A1* | 12/2017 | Raby | A61C 7/36 |

* cited by examiner

COMPUTER IMPLEMENTED METHOD FOR MODIFYING A DIGITAL THREE-DIMENSIONAL MODEL OF A DENTITION

CROSS-REFERENCE TO RELATED APPLICATIONS

This application claims priority to and is a continuation application of U.S. Ser. No. 16/278,444 filed Feb. 18, 2019, which claims priority to European patent application No. 18157574.7 filed on Feb. 20, 2018, European patent application No. 18157809.7 filed on Feb. 21, 2018, and European patent application No. 18197512.9 filed on Sep. 28, 2018, all the disclosures of which are incorporated herein by reference in their entirety.

TECHNICAL FIELD

The present invention relates to a computer implemented method for modifying a digital three-dimensional model of a dentition comprising: displaying an image of the dentition on a display; receiving user input information modifying the shape of at least a portion of the dentition by markings input on the image on the display; and transferring the shape modifying information to the three-dimensional model and modifying the three dimensional model accordingly.

The three-dimensional model of the dentition has usually been obtained by either using a library of dentitions or by scanning and/or phototechnical acquisition of the oral cavity of a person, or by scanning the shape of the dentition taken as impressions in casting compound material in impression trays.

The invention may be used in a dental Augmented Reality application to preview a dental situation, which is the result of any modification of the dentition e.g., after a planned dental treatment, with teeth position correction devices in place or including any other modification of the dentition. The modified state of the dentition of the patient (e.g. after dental treatment) is referred to as the dental situation in the present application. The dental treatment can be planned using computer-implemented dental treatment design tools starting from the three-dimensional model of the dentition and creating a modified three-dimensional model of a dental situation after the treatment. Another option is to create a physical model of the dentition and to modify it by any dental alteration to obtain a physical model of the planned dental situation which is then scanned. The planned dental situation may include one or more new dental prostheses or other dental restorations, or a corrected teeth arrangement as a result of corrections of teeth positions, for example by use of dental braces.

For dentists, dental technicians and patients, it is of interest to get a visual impression of the appearance of a modified dental situation, i.e. to visualize the modified dental situation in an image of the face of the patient. For this purpose, a virtual preview (virtual mock-up) of the dentition modified by dental treatment is helpful for the dentist and may also be used in the course of interactively modifying the dental situation to get the most favorable aesthetic results.

BACKGROUND

U.S. Pat. No. 9,775,491 B2, which is hereby incorporated by reference in its entirety, discloses a computer implemented method for visualizing an image rendered from a three-dimensional model of a dental situation to an image of the face of the patient recorded by a camera. In this method a three-dimensional model of the oral cavity of the patient is obtained. This three-dimensional model is modified in a dentistry treatment plan by applying dental restorations to obtain a three-dimensional model of the dental situation of the patient dentition after application of the dental restorations. A two-dimensional image of the face of the patient including the mouth opening is obtained. Then the positioning of the camera that recorded the image relative to the dentition of the patient is estimated. In this application "positioning of the camera" meant to include the three-dimensional position x, y, z in space and the angular orientation of the camera with respect to the face of the patient. A virtual camera using the estimated positioning is processing the three-dimensional model of the dental situation to obtain a two-dimensional image, and a portion of the three-dimensional model of the dental situation is selected which is visible to the virtual camera. The image rendered by the virtual camera is overlaid and displayed in the image taken by the camera.

Similar methods are set forth in US 2011212420 directed to a method of forming a dental mold, US 20130060532 directed to a method of composing and designing teeth, US 2013158958 directed to a dental analysis method and system and US 20170319293 directed to a method of digitally designing a modified dental setup, all of which are hereby incorporated by reference in their entirety.

U.S. Pat. No. 7,717,708 B2, which is hereby incorporated by reference in its entirety, describes computer-based methods for supporting dentists during dental treatment planning for a patient. In such a method various sources of information on the physiological and anatomical state of the dentition of the patient are stored in the computing device. This includes for example a three-dimensional model of the dentition including the upper and lower teeth arches and gingiva, as well as two-dimensional images of the patient recorded by a camera, including the mouth opening and the visible parts of the dentition therein. The photo of the mouth opening may be displayed on a display of the computing device, and the dental practitioner may use software tools for marking certain features in the displayed photo, for example the occlusal plane. Furthermore, it is mentioned that software tools are provided for simulating changes in the anatomical position or shape of the craniofacial anatomical structures and their effect on the external visual appearance of the patient. In this connection it is also mentioned that any changes or modifications applied to the displayed photo of the dentition are automatically transferred to the three-dimensional model of the dentition which is modified accordingly. For marking certain features and lines on the displayed photo it is described that the user identifies points and lines with a user interface such as a mouse on the display. For marking a line or curve in the image of the dentition it is therefore necessary to input a plurality of points along the curve using the mouth. One important aspect when planning restorations for a part of or a complete dental arch is the positioning of the visible teeth arch contour curves, namely the incisal curve and the gingiva border curve of the upper and lower teeth arches, in the image of the mouth opening of the patient. Point by point input of such curves in the path of the upper or lower teeth arch to receive dental restorations is a slow and inefficient procedure.

In particular, when designing restorations for the upper or lower teeth arch the positioning of the visible teeth arch contour lines in the mouth opening is an important aspect. In this respect it would be particularly useful to get an immediate visualization of a modified incisal curve or a modified gingiva teeth border curve.

SUMMARY OF THE INVENTION

It is an object of the present invention to provide a method for modifying a digital three-dimensional model of a dentition of a person. The method allows for a quick intuitive input of a modification of the positioning and shape of a visible teeth arch contour curve of the upper or lower teeth arches.

These objects are achieved by the method comprising the features of the claims. Preferred embodiments of the invention are set out in the dependent claims.

According to the present invention the user can modify one of the visible teeth arch contour curves (incisal curve or gingiva border curve) by drawing or sketching a new line on the image of the dentition on the display, wherein the line drawn on the display determines up to where the new teeth arch contour curve should extend. It should be noted that the line drawn on the display is not shown on the display but only serves input information. The user can draw the line with his finger by sliding his finger tip along the new curve, or use an input tool such as pen to draw the new line on the display; again it should be noted that there is no physical line remaining or displayed in any way on the display. The display can be a touch screen which acquires the line drawn; alternatively the input tool can be a mouse, stylus or the like which can be used to draw a line by moving a cursor controlled by the mouse along the display or drawing a line with the stylus. In other words, along the line the teeth are stretched/compressed in the image in length direction (between tooth root and incisal edge) in the region of the line such that the teeth extend between the projected line and the dental arch contour curve opposite to the dental arch curve which is modified by the line drawn. This modification of the dental arch is done by deforming the three-dimensional model of the dentition in accordance with the line drawn.

In order to allow such design modifications by drawing virtual lines on the display displaying the dentition the following steps are performed. The image of the dentition is obtained by applying a virtual camera to the three-dimensional model of the dentition to render a two-dimensional image which is displayed on the display. The line drawn by the user on the image on the display is acquired and further processed. For this purpose the same virtual camera (i.e. in the same camera positioning) that was used to render the two-dimensional image of the dentition is used to project the acquired line to a three-dimensional projection surface which is approximating the shape of the upper and lower dental arches in the three-dimensional model of the dentition and which extends the dental arches into the adjoining gingiva regions and in the direction towards the other teeth arch to cover any opening between the upper and lower dental arches.

In the three-dimensional model of the dentition visible teeth arch contour curves of the upper and lower teeth arches are obtained, namely the incisal curve and the gingiva border curve for each of the upper and lower teeth arches. The teeth arch contour curves may be obtained by deriving them from the three-dimensional model of the dentition by automatic line detection in the three-dimensional model, or can be predefined by a user in advance. The teeth arch contour curves are then projected to the projection surface. One way of projection is to represent the curves as line segments where each point is projected by finding the closest point on the projection surface, respectively. Connecting these projected points results in the projected curves.

One of the teeth arch contour curves is selected as the one to be modified. This is done either based on a user selection in advance or can be done for example by selecting the one of the teeth arch contour curves which is closest to the projected line on the projection surface. The distance between two curves can for example be defined by calculating the integral over the projection surface area between the two curves.

All teeth along the projected line which belong to the selected teeth arch contour curve are deformed in the three-dimensional model of the dentition in a length direction of the teeth such that at least parts of the selected teeth arch contour curve, after deformation and projection to the projection surface, coincide with the projected line and any remaining parts of the selected teeth arch contour curve are located between the projected line and the baseline curve, whereas teeth regions on and beyond the baseline curve remain unaffected by the deformation.

That means that the acquired line projected to the projection surface becomes an enveloping or maximum line of the modified teeth arch contour curve, and, when the teeth arch contour curve to be modified is an incisal curve, the teeth in the affected area of the teeth arch are deformed by stretching or compressing them (stretching when the line drawn is further away from the gingiva border curve, and compressing when the line drawn for the new incisal curve is closer to the gingiva border curve than the current incisal curve). In this manner the teeth along the projected line are elongated or compressed in a manner defined by the line drawn on the image of the dentition on the display.

In the same manner the gingiva border curve can be redesigned by drawing a corresponding line, wherein in this case the opposite incisal curve of the same teeth arch is the baseline curve, and the teeth are elongated or compressed along the line drawn such that the gingiva border curve of the deformed teeth contacts the line drawn, whereas the opposite incisal curve remains unaffected.

As regards the deformation of the three-dimensional model of the dentition this includes methods in which a deformed three-dimensional model is generated and the original (undeformed) three-dimensional model is kept and remains stored.

The deformation of the three-dimensional model of the dentition can for example be carried out by applying scaling factors multiplying all coordinate values in the direction of deformation of all points of the three-dimensional model. For example, in case a polygon mesh is used for the three-dimensional model all vertices of the polygon mesh can be scaled using a scaling factor for the coordinate to be deformed, wherein the origin of the coordinate to be deformed is defined by the baseline curve such that no deformation takes place at the baseline curve itself, and the deformation in absolute terms is more pronounced the further the coordinate point is spaced apart from the zero line (baseline curve).

In a preferred embodiment the baseline curve is derived from the other teeth arch contour curve of the same teeth arch as the teeth contour curve to be modified by smoothing the other teeth arch contour curve. Smoothing of curves can be achieved as described above. Another possibility is to define a neighborhood range and assign an average or a maximum value within the neighborhood range.

In a preferred embodiment the deformation along the projected line is completed, and then an image of the deformed three-dimensional model is rendered by applying the virtual camera to the deformed three-dimensional model and the rendered image is displayed on the display instead of the image of the original undeformed three-dimensional model (the image thereof). In this manner the user can immediately get an impression of the visual appearance of the modified design of the dentition.

Alternatively new images are rendered continuously in real-time while the line is drawn on the display and the rendered images of the deformed portion of the selected teeth arch contour curve are displayed in real-time up to the current point to which the line has been drawn. In this case the image of the deformed teeth arch portion is following the line while this line is continued to be drawn by the user on the display. For example, the user can first draw a first line portion for defining a first part of a modified teeth arch contour curve, and the resulting modified portion of the teeth arch is already displayed by rendering the deformed three-dimensional model, and then the user can continue to draw the line to a further portion of the teeth arch to complete the design of the selected teeth arch contour curve. In principle, when the user first draws a short line portion this may have the effect that only a part of the teeth contour curve may be deformed by drawing a line only along a portion of a single tooth which then would already have the effect that only the incisal curve or gingiva border curve of this part of the tooth would be modified and the modified design be displayed on the display.

In a preferred embodiment the user may select the teeth arch contour curve to be modified by a line to be drawn in advance by explicitly identifying a particular teeth arch contour curve, or the teeth arch contour curve to be modified is automatically selected by selecting the teeth arch contour curve that is closest to the projected line when no other selection is present.

In a preferred embodiment the projected line is formed from the acquired line by using a sequence of points along the acquired line, and for each point by projecting, using the virtual camera, a straight line that intersects the point on the acquired line to the projection surface and by determining the intersection point of the straight line with the projection surface, wherein the projected line is formed by connecting the sequence of intersection points on the projection surface. In other words the acquired line is described by a polyline, and points along the polyline are projected by the virtual camera projecting a straight line through each point of the polyline on the display by the virtual camera to the projection surface to determine its position relative to the teeth arches. The sequence of intersection points with the projection surface formed in this manner describes the projected line as a polyline on the projection surface. The projection surface is needed in particular in the situation when the projected line would not be intersecting with any part of the dentition, e.g. the projected line is extending in an open area between the incisal curves of the upper and lower teeth arches.

In a preferred embodiment a vertical direction is defined for the three-dimensional model of the dentition by a direction perpendicular to an occlusal plane of the three-dimensional model of the dentition. The projection surface is then defined by a surface of a sector of a right cylinder or right prism around an axis parallel to the vertical direction, i.e. the longitudinal axis perpendicular to the end faces of the right cylinder or right prism is oriented in vertical direction. The projection surface is subdivided into a plurality of subsectors, each subsector extending over an incremental angular step with respect to the longitudinal axis of the cylinder or prism sector. For each subsector at least one point of the projected line is determined by projection or interpolation of projected points from neighboring sectors. For each subsector a corresponding dentition model subsector is determined by determining all coordinate points in the three-dimensional model contained in the subsector of the right cylinder or right prism sector. The deformation is performed for all coordinate points within the dentition model sector by applying a scaling factor scaling all coordinate points within the subsector in vertical direction, wherein the scaling factor is determined for each subsector separately. In this manner the projection surface and the scaling of the three-dimensional model of the dentition is discretized and performed in incremental subsectors along the projected line on the projection surface separately.

In a preferred embodiment the deformation is performed in the following manner. In each subsector on the projection surface a first point on the projected line and a second point vertically aligned with the first point are selected, which second point is the intersection point of a vertical line extending from the first point with the selected teeth arch contour curve projected to the projection surface. First and second vertical distances between the baseline curve of the three-dimensional model of the dentition projected to the projection surface and the first and the second point, respectively, are determined. The ratio between the first and second distance is calculated as the scaling factor for the subsector. If, for example, the point of the projected line has a vertical distance to the baseline curve of 11.0 mm, and the projected incisal curve of the selected teeth arch has a distance of 10.0 mm to the baseline curve, then the scaling factor for this subsector is 1.1.

For example, the first point of the subsector can be the one which has the maximal vertical distance of the projected line to the baseline curve in the subsector.

In particular, the deformation in each subsector can be performed using the scaling factor in the following manner. All coordinate points of the three-dimensional model of the dentition are multiplied by the scaling factor of the subsector by multiplying a z-coordinate, being defined in the vertical direction, of each coordinate point within the subsector with the scaling factor of the subsector, wherein the average value of the z-coordinate of the baseline curve defines the value zero of the z-coordinate in the subsector and only coordinate points with $z>0$ are scaled by multiplication with the scaling factor. In this manner coordinate points with z-coordinates closed to the baseline curve will be stretched/compressed by a small absolute amount only since the z-coordinate value itself is small, whereas coordinate points closed to the selected teeth arch curve will undergo a larger absolute deformation bringing them to or closed to the projected line.

In a preferred embodiment the selected teeth arch contour curve is smoothed by damping rapid changes along the teeth arch contour curve. Smoothing of the curves can for example be achieved by applying a filter, for example a low pass filter for damping rapid changes along the curve, or by fitting parameters included in a predetermined function so that the fitted function approximates the selected teeth arch contour curve by a smooth curve. In a preferred embodiment the baseline is derived from the opposite teeth arch contour curve of the same teeth arch by smoothing the curve to obtain the baseline curve.

In a preferred embodiment the selected teeth arch contour curve projected to the projection surface is used to select a teeth arch contour point for each subsector, for example a central point in the subsector. The teeth arch contour curve is then smoothed by defining in each subsector the teeth arch contour point by selecting it from a range of a predetermined number of neighboring subsectors as the teeth arch contour point having the largest vertical distance to the baseline curve. This smoothing by selecting the maximal distance point from a neighborhood of for example two or three neighboring subsectors is particularly useful for the incisal curve because in this manner the valleys or recesses of the incisal curve in the regions of adjoining neighboring teeth is at least partly preserved, i.e. also after deformation, for example by stretching teeth to elongate them there are still valleys in the resulting incisal curve in the adjoining region of a pair of neighboring teeth.

In a preferred embodiment, if the selected teeth arch contour curve that is to be modified is a gingiva border curve, the adjoining gingiva border region in the three-dimensional model of the dentition is deformed locally to adapt it to the deformation of the teeth determined by the projected line, wherein local deformation in vertical direction is performed in a manner such that movement of the coordinate points in vertical direction due to the deformation becomes smaller the further the coordinate points are spaced apart from the unmodified gingiva border curve.

In a preferred embodiment, in each subsector of the projection surface a first point of the projected line and second point vertically aligned with the first point are selected which second point is the intersection point of a vertical line extending from the first point with the smoothed teeth arch contour curve, first and second vertical distances between the baseline curve and the first point and the second point, respectively, are determined, and the ratio between the first and second distance is calculated as the scaling factor for the subsector.

Instead of the local deformation by a scaling factor a translation of the coordinates in vertical direction can be carried out, wherein a translation equal to the vertical distance between the old and the new curve is selected and is weighed with a weight factor which is close to 1 for coordinates close to the old curve and which is 0 close to the baseline curve.

BRIEF DESCRIPTION OF THE DRAWINGS

The invention will in the following be described with reference to the accompanying drawings in which.

DETAILED DESCRIPTION

Figure 1:
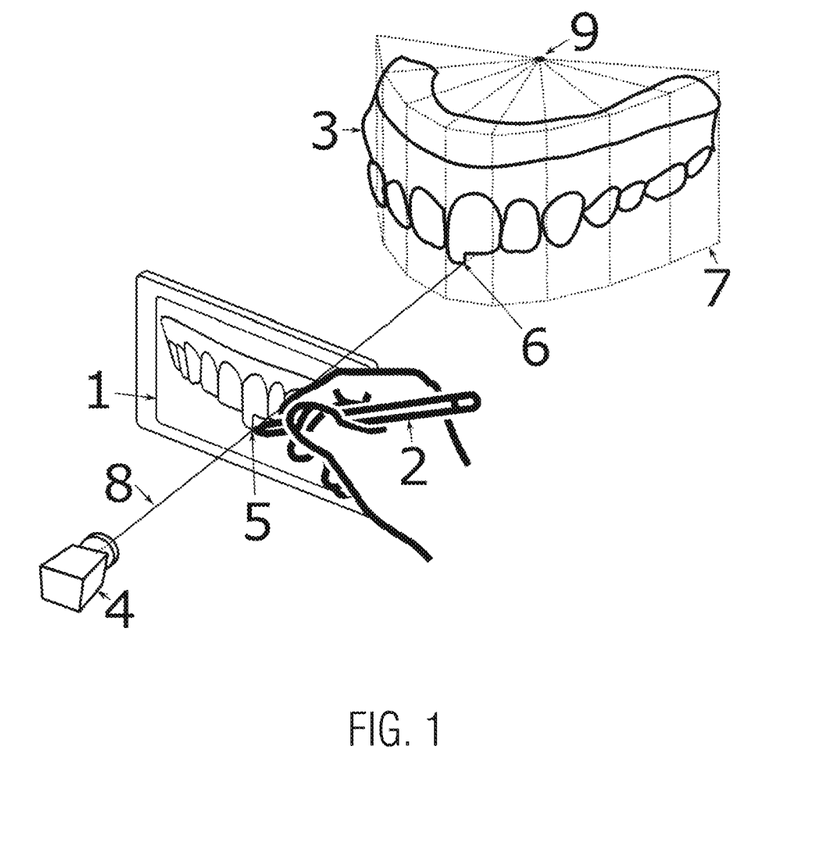
FIG. 1 is a schematic illustration for illustrating principles of the method of the present invention.

FIG. 1 gives a schematic overview over elements used in the method according to the invention. In a computing device a three-dimensional model of a dentition 3 is stored. The three-dimensional model of the dentition may for example be in the format of a polygon mesh with polygons as surface elements of the three-dimensional model as shown in the schematic illustration of the three-dimensional model of the dentition in FIG. 3. In the computing device various software modules are stored that, when executed, perform the steps of a method according to the present invention. One of the software modules is a virtual camera 4. This virtual camera 4 is on the one hand used for rendering a two-dimensional image from the three-dimensional model of the dentition 3. The two-dimensional image of the dentition rendered by the virtual camera 4 is displayed on a display 1 connected to the computing device.

As shown in FIG. 1 a user slides the tip of a pencil on the display 1 to draw an invisible line in the two-dimensional image of the dentition, i.e. no physical line is drawn but the information where the pencil tip moved along is acquired and used for a real-time deformation of the 3D model of the dentition.

To simplify the illustration FIG. 1 only shows the upper teeth arch of the three-dimensional model of the dentition, whereas a three-dimensional model of the dentition in general also includes a lower teeth arch of the dentition.

The line drawn by the user on the display with the two-dimensional image of the dentition is acquired by the computing device, either by acquiring the continuous line or by acquiring a polyline representing the line drawn by a sequence of points acquired along the line drawn.

The user draws the line on the display with the image of the dentition in order to modify one of the visible teeth arch contour curves, i.e. either the incisal curve defined by the incisal edges of the teeth in the teeth arch or the gingiva border curve.

In order to modify the three-dimensional model of the dentition according to the line drawn to define a new teeth arch contour curve the following steps are performed. The virtual camera 4, which is used using the same positioning as for rendering the two-dimensional image from the three-dimensional model of the dentition 3 on the display 1, is used to project a straight line 8 passing through the contact point 5 of the tip of the pencil on the display to a projection surface 7 to determine a projected line point 6. The projection surface 7 is needed to define the position of the projected point in three-dimensions. In the area of the teeth arch the projection surface approximates the shape of the teeth arch and extends it in vertical direction, perpendicular to the occlusal plane of the dentition, to surface areas above and below the teeth arch. The projection surface can for example be formed by a sector of a right cylinder or, as shown, of a right prism. The right prism has a vertical longitudinal axis 9 perpendicular to the occlusal plane. The right prism having a front outer surface defining the projection surface 7 is subdivided into a plurality of subsectors, each subsector extending over an incremental angular step with respect to the longitudinal axis 9 of the prism sector. In the simplified illustration of FIG. 1 the size of the subsectors is exaggerated for simplification. It is preferred to subdivide the projection surface in much finer subsectors which are small compared to the width of a tooth, and not of the same order as the width of the teeth as in FIG. 1.

While the user draws the line on the display a corresponding projected line on the projection surface is continuously formed which progresses along the projection surface 7 as the tip of the pen progresses along the line on the display. The line drawn on the display is used to modify a visible teeth arch contour curve of one of the upper and lower teeth arches in the three-dimensional model 3 of the dentition, in the example illustrated of the upper teeth arch. The selected teeth arch contour line to be modified is in this example the incisal curve of the upper teeth arch. Which teeth arch contour curve is to be modified by the line drawn may for example be defined by a user input in advance identifying the teeth arch contour line to be modified. Alternatively, the teeth arch contour line which is next to the drawn line may be automatically selected as the teeth arch contour curve to be modified.

The projected line resulting from a sequence of projected line points 6 on the projection surface is then used to deform the teeth of the three-dimensional model along the projected line so that the selected teeth arch contour curve, in this case the incisal curve of the upper teeth arch, is moved towards the projected line so that at least parts of the modified incisal curve are coinciding with the projected line, whereas the remaining parts of the incisal curves are between the projected line and the opposite baseline curve, in this case the gingiva border curve of the upper teeth arch. In other words the projected line defines a border line or limiting line for the modified incisal curve of the upper teeth arch.

Figure 2:
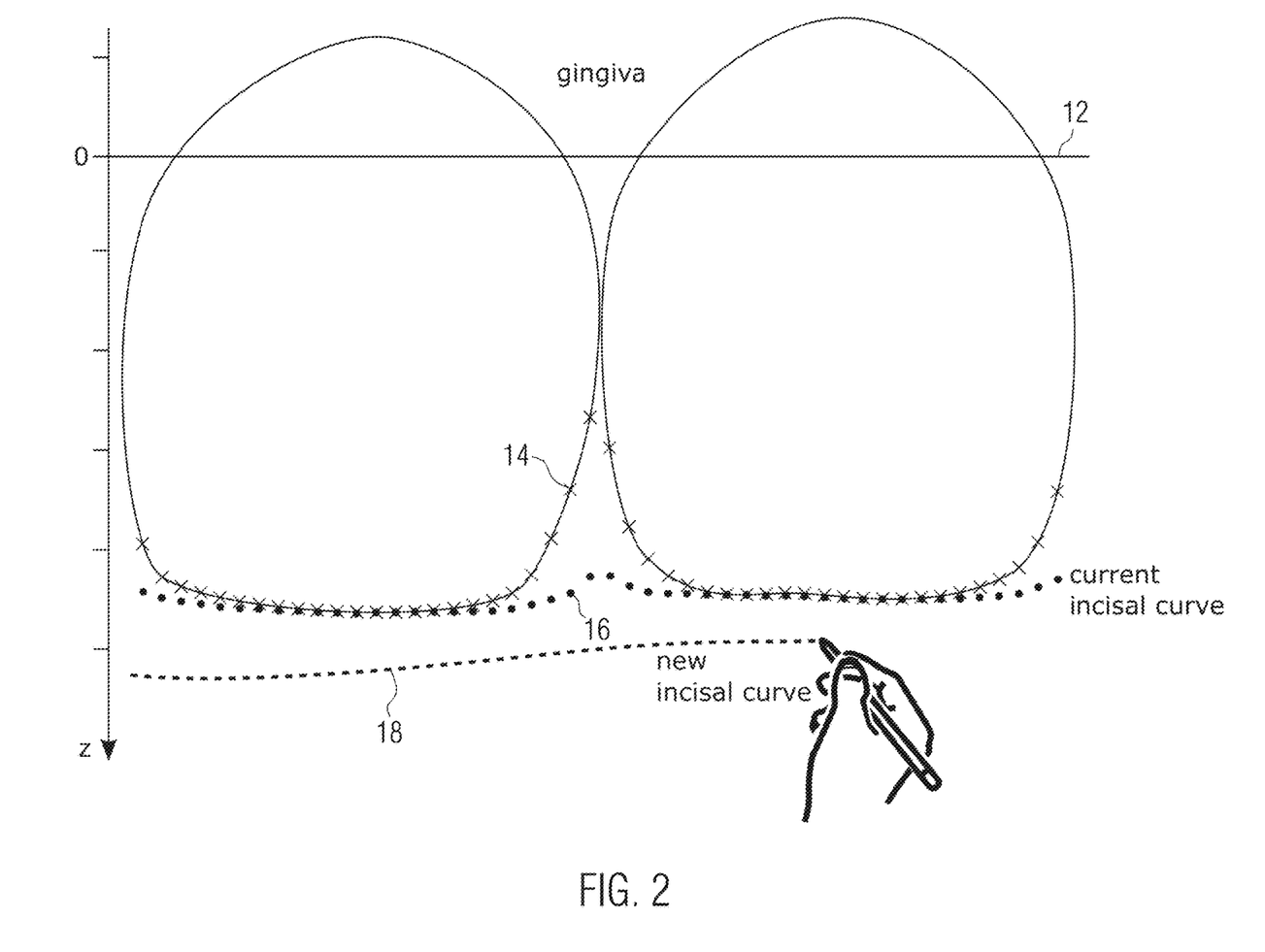
FIG. 2 is a schematic illustration of a part of an upper teeth arch illustrating various curves and points used in a preferred embodiment of the method of the present invention.

An example, how the teeth can be deformed in such a manner will be described with reference to FIG. 2. FIG. 2 shows a partial view of the upper teeth arch, namely a pair of neighboring teeth. A gingiva border contour curve 12 is shown as a smoothed curve derived from the three-dimensional model of the dentition. The basis of each of the two teeth extends into the gingiva. The gingiva border contour curve in this case forms the baseline curve. The incisal curve is derived from the three-dimensional model of the dentition, and is projected onto the projection surface. The projected incisal curve is represented by a sequence of crosses 14, each cross 14 representing an incisal curve point from one of the subsequent subsectors of the projection surface. As can be seen by comparison with FIG. 1, the width of the subsequent subsectors in the example of FIG. 2 is much smaller and significantly smaller than the width of a tooth. The cross 14 from each subsector may for example represent the incisal curve point from this subsector having the largest vertical distance to the baseline 12. It should be noted that both the baseline 12 as well as the sequence of crosses 14 representing the incisal curve derived from the three-dimensional model of the dentition are projected onto the projection surface 7. This also applies to the projected line 18 which represents the acquired line drawn on the display projected by the virtual camera 4 to the projection surface 7. In addition to the incisal curve 14 a smoothed incisal curve is shown in FIG. 2 represented by a sequence of dots 16. This smoothed incisal curve in which rapid changes along the curve are damped is formed in this example in the following manner. For each subsector the two neighboring subsectors in each direction are taken into account and the incisal curve point of the range of neighboring subsectors taken into account is selected as the incisal curve point for the present subsector which has the largest vertical distance to the baseline 12. In this manner the recess in the adjoining region of the neighboring teeth is diminished compared to the incisal curve represented by the crosses 14.

For each of the subsequent subsectors now a scaling factor is determined by comparing the vertical distances between the projected curve 18 and the baseline curve of the one hand, and between the smoothed incisal curve represented by the dots 16 and the baseline curve 12 on the other hand. In particular, a ratio between the distances mentioned is determined for each subsector as a vertical scaling factor which is then used to deform the tooth region corresponding to this subsector in the three-dimensional model of the dentition by applying the scaling factor. As can be seen from FIG. 1 each subsector also defines a corresponding sub-volume in the three-dimensional model of the dentition. For each subsector all coordinate points of the three-dimensional model of the dentition are subjected to the scaling factor determined for the subsector by multiplying the vertical z-coordinate of each of the coordinate points with the scaling factor of the subsector. In this manner point on the baseline curve are not affected by the deformation, whereas the absolute shift in z-direction is the larger the further a coordinate point is away from the baseline curve in z-direction. In this manner the apex region of the incisal curve of a tooth is moved to touch the projected line 18.

The recessed region in the adjoining area of neighboring teeth instead is not completely deformed to the projected line 18 but the recessed shape is partly maintained within these regions in which the recessed region being located between the projected line 18 and the baseline curve 12. This behavior is intended in a preferred embodiment because in this manner the modified incisal curve to a certain extent maintains the recesses in the adjoining region of a pair of neighboring teeth. The reason why the recesses are partly maintained is that the smoothed incisal curve 16 has been used to determine the scaling factors. The smoothed incisal curve results in the recess region in the adjoining area of a pair of neighboring teeth in relatively smaller scaling factors as would have resulted when the scaling factors had been determined from a comparison of the projected line 18 and the incisal curve 14.

Figure 3:
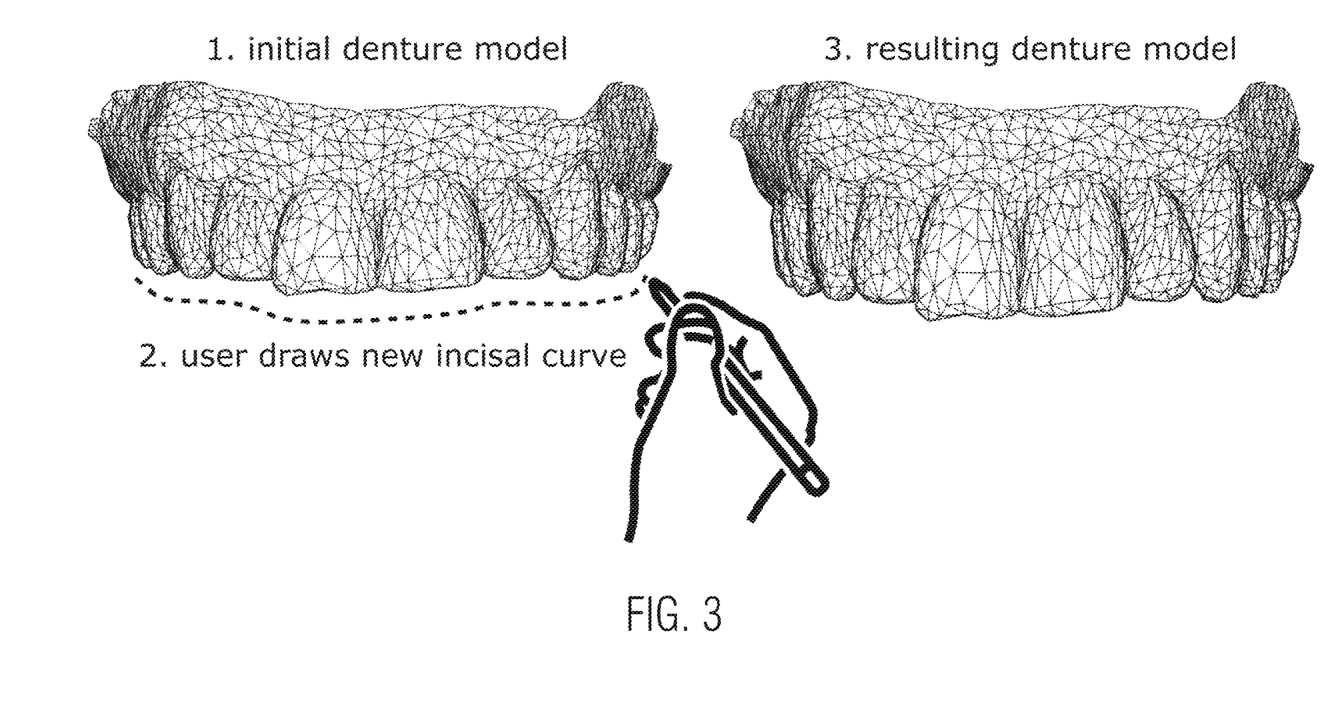
FIG. 3 is a schematic illustration showing a three-dimensional model of a dentition, a line drawn by a user on the display showing the image of the dentition, and the resulting modified three-dimensional model of the dentition rendered after performing the deformation of the teeth to modify the incisal curve.

The effect of the deformation effected as described by using vertical scaling factors determined for each subsector is illustrated in FIG. 3. FIG. 3 shows on the left hand side the three-dimensional model of dentition in the original state, here represented by a polygon mesh. Also shown is the line drawn by the user to illustrate in which direction and to what extend the user wants to modify the three-dimensional model of the dentition by modifying the incisal curve of the upper teeth arch. When applying the scaling factor for each subsectors as determined as described in connection with FIG. 2 to all coordinate points (vertices) of the polygon mesh falling in this angular subsector by multiplying the z-coordinates with the respective scaling factor, the teeth along the projected line are deformed towards the projected line as shown on the right hand side of FIG. 3. In absolute terms this shifts coordinate points which are closer to the projected line to a larger extent by stretching them towards the projected line, whereas the vertical or movement of coordinate points gets smaller the smaller the distance to the baseline curve becomes. At the baseline curve itself no deformation takes place so that the baseline curve itself remains in place in the three-dimensional model.

In the context of the present invention, the term "denture" is not necessarily restricted to full dentures but also comprises partial dentures or orthodontic situation/adaptations or dental restorations such as dental prostheses, including crowns, crown lays, veneers, inlays and onlays, bridges, dental implants, implant restorations. Accordingly, the term "dental model" includes all models of dental prostheses as well as the patient situation that could be partial or fully edentulous—such as models of complete and partial dentures—that are used for prosthodontic purposes.

In some embodiments, the present disclosure is implemented using a system having a camera, a processor, an electronic data storage unit, and a display. The camera can be a standard camera, an infrared dot-projection detector, flood illuminator camera, structured-light three-dimensional scanner, standard infrared detector, ultrasonic imaging device, Doppler detector, or any other suitable visualization system capable of capturing information related to a patient's dentition. The processor can be a single processor having one or more cores, or a plurality of processors connected by a bus, network, or other data link. The electronic data storage unit can be any form of non-transitory computer-readable storage medium suitable for storing the data produced by the system. The display can be any display suitable for displaying a digital color or grayscale image.

In some embodiments, the camera, processor, electronic data storage unit, and digital display are components of a single device. The single device may be a smartphone, tablet, laptop computer, personal digital assistant, or other computing device.

In some embodiments, the processor is in communication over a network, which could be wired or wireless, with an external processor used for performing one or more calculation steps and/or a network-attached electronic data storage unit. In some embodiments, the present disclosure makes use of cloud computing to perform one or more calculations steps remotely and/or remote storage to enable the storage of data remotely for collaborative or remote analysis. In some embodiments, the system comprises a plurality of graphical user interfaces to permit multiple users to view or analyze the same data.

In some embodiments, the system operates to provide one or more users with a visualization of a virtual dental model of a patient's teeth, which may be altered to visualize the effect of one or more dental or orthodontic alterations. In some embodiments, this allows the one or more users to visualize a "before" dentition image, i.e., the appearance of a patient's dentition prior to a dental or orthodontic procedure, and an "after" dentition image, i.e., a representation of the expected appearance of a patient's dentition after a proposed dental or orthodontic procedure.

In some embodiments, the system operates by capturing information related to a patient's dentition using a camera, creating a model of the patient's dentition on a processor, fitting a model of a proposed post-alteration dentition to the patient's dentition on the processor, coloring the model of the proposed post-alteration dentition to match an expected real post-alteration coloration, and displaying the fitted model of the proposed post-alteration dentition in place of the patient's actual dentition on a display which otherwise shows the patient's actual facial features. The information related to a patient's dentition, the model of the patient's dentition, and the model of the proposed post-alteration dentition may be stored on an electronic data storage unit. In some embodiments, the operations are performed in real-time.

In some embodiments, a user interface is configured such that a user may view the "before" dentition image and the "after" dentition image simultaneously either side-by-side or with a full or partial overlay.

Where used herein, the term "non-transitory" is a limitation on the computer-readable storage medium itself—that is, it is tangible and not a signal—as opposed to a limitation on the persistence of data storage. A non-transitory computer-readable storage medium does not necessarily store information permanently. Random access memory (which may be volatile, non-volatile, dynamic, static, etc.), read-only memory, flash memory, memory caches, or any other tangible, computer-readable storage medium, whether synchronous or asynchronous, embodies it.

Although the invention is illustrated above, partly with reference to some preferred embodiments, it must be understood that numerous modifications and combinations of different features of the embodiments can be made. All of these modifications lie within the scope of the appended claims.

The invention claimed is:

1. A computer implemented method for modifying a digital three-dimensional model of a dentition comprising:
    rendering a two-dimensional image of the three-dimensional model of a dentition onto a display,
    selecting a gingiva contour curve or an incisal contour curve as a baseline curve,
    selecting the gingiva contour curve or the incisal contour curve that is not selected as the baseline curve, as the selected contour curve to be modified,
    receiving user input information for modifying a shape of the two-dimensional image, said user input information comprising acquiring a line drawn by the user on the two-dimensional image on the display for the selected contour curve to be modified,
    projecting the acquired line using a virtual camera to provide a projected line and applying the projected line onto a three-dimensional projection surface approximating a shape of a dental arch in the digital three-dimensional model of dentition,
    deforming all teeth belonging to the selected contour curve to be modified along the projected line in the three-dimensional model of the dentition in a length direction such that at least parts of the selected contour curve, after deformation and projection to the projection surface, coincide with the projected line and any remaining parts of the selected contour curve are located between the projected line and the baseline curve, whereas the baseline curve remains unaffected by the deformation.

2. The computer implemented method according to claim 1,
    wherein the three-dimensional model of the dentition comprises incisal and gingiva border curves corresponding to the incisal contour and gingiva contour curves of the two-dimensional image, said incisal and gingiva border curves projected to the projection surface.

3. The computer implemented method according to claim 1,
    wherein after deformation of the teeth of the selected contour curve to be modified is completed, an image of the deformed three-dimensional model is rendered by applying the virtual camera and the rendered two-dimensional image is displayed on the display.

4. The computer implemented method according to claim 1,
    wherein the deformation of the teeth of the selected contour curve to be modified is continuously progressing and following the currently drawn line portion while the line is drawn in real-time and the rendered image of the deformed portion of the selected contour curve to be modified is displayed in real-time up to the current point to which the line has been drawn.

5. The computer implemented method according to claim 1,
    wherein one of the contour curves is selected by user input or by selecting the contour curve that is closest to the acquired line when no other selection is present.

6. The computer implemented method according to claim 1,
    wherein for forming the projected line from the acquired line a sequence of points along the acquired line is used and for each point a straight line that goes through this point along the acquired line is projected, using the virtual camera, to the projection surface and an intersection point of the straight line with the projection surface is determined, wherein the projected line is formed by connecting the sequence of intersection points on the projection surface.

7. The computer implemented method according to claim 1,
wherein a vertical direction is defined for the three-dimensional model of the dentition by a direction perpendicular to an occlusal plane of the three-dimensional model of the dentition,
wherein the projection surface is defined by a surface of a sector of a right cylinder or right prism, wherein the longitudinal axis of the cylinder or prism is parallel to the vertical direction,
wherein the projection surface is subdivided into a plurality of subsectors, each subsector extending over an incremental angular step with respect to the longitudinal axis of the cylinder or prism sector,
wherein at each subsector at least one point of the projected line is determined,
wherein for each subsector a corresponding dentition model subsector in the three-dimensional model of the dentition is determined by determining all coordinate points in the three-dimensional model contained in the subsector, and
wherein the deformation is performed for all coordinate points within the dentition model sector by applying a scaling factor scaling all coordinate points in vertical direction, which scaling factor is determined for each subsector separately.

8. The computer implemented method according to claim 7,
wherein in each subsector of the projection surface a first point of the projected line and second point vertically aligned with the first point are selected which second point is the intersection point of a vertical line extending from the first point with the selected contour curve to be modified of the three-dimensional model of the dentition projected to the projection surface, first and second vertical distances between the baseline curve of the three-dimensional model of the dentition projected to the projection surface and the first point and the second point, respectively, are determined, and the ratio between the first and second distance is calculated as the scaling factor for the subsector.

9. The computer implemented method according to claim 8,
wherein for performing the deformation in each subsector the determined scaling factor is applied by multiplying a z-coordinate, being defined in the vertical direction, of each coordinate point within the subsector with the scaling factor of the subsector, wherein the average value of the z-coordinate of the baseline curve defines the value 0 of the z-coordinate in the subsector.

10. The computer implemented method according to claim 1,
wherein the selected contour curve to be modified is smoothed by damping rapid changes along the selected contour curve.

11. The computer implemented method according to claim 10,
wherein the selected contour curve to be modified is used to select a contour point for each subsector, in that the contour curve is smoothed by defining in each subsector the contour point by selecting said point from a range of a predetermined number of neighboring subsectors as the contour point having the largest vertical distance to the baseline curve.

12. The computer implemented method according to claim 1,
wherein the baseline curve is derived from the contour curve opposite to the selected contour curve to be modified of the same teeth arch by smoothing the opposite arch contour curve.

13. The computer implemented method according to claim 1,
wherein, if the selected contour curve to be modified is a gingiva border curve the adjoining gingiva border region is deformed locally to adapt it to the deformation of the teeth determined by the projected line, wherein local deformation in a vertical direction is performed in a manner such that movement of the coordinate points in vertical direction due to the deformation becomes smaller the further the coordinate points are spaced apart from the unmodified gingiva border curve.

14. The computer implemented method according to claim 7,
wherein in each subsector of the projection surface a first point of the projected line and second point vertically aligned with the first point are selected which second point is the intersection point of a vertical line extending from the first point with the smoothed contour curve, first and second vertical distances between the baseline curve and the first point and the second point, respectively, are determined, and the ratio between the first and second distance is calculated as the scaling factor for the subsector.

15. The computer implemented method according to claim 1,
wherein approximating the shape of the dental arch in the digital three-dimensional model of dentition comprises extending the shape in a length direction of the teeth of the dental arch.

* * * * *